United States Patent [19]

Pigerol et al.

[11] 4,299,768
[45] Nov. 10, 1981

[54] 1-PYRROLE- AND 1-PYRROLIDINE-CARBOXYLIC ACID DERIVATIVES AND PROCESS FOR PREPARING THE SAME

[75] Inventors: Charles Pigerol, Saint-Ouen; Michel Schaefer, Metz, both of France; Souli Nanthavong, Vientiane, Laos

[73] Assignee: LABAZ, Paris, France

[21] Appl. No.: 47,585

[22] Filed: Jun. 11, 1979

[30] Foreign Application Priority Data

Jun. 12, 1978 [FR] France ................... 78 17424

[51] Int. Cl.³ .................. C07D 207/22; C07D 207/10
[52] U.S. Cl. .............................. 260/326.25; 260/326.4
[58] Field of Search ......................... 260/326.25, 326.4

[56] References Cited

PUBLICATIONS

M. Shamma et al., Tetrahedron 1973 29(14) pp. 1949-1954.
W. Bartmann et al., Chem. Abstracts 86: 155508w (1977).
H. Rapoport et al., J. Amer. Chem. Soc., 84 2178-2181, 630 (1962).

Primary Examiner—Donald G. Daus
Assistant Examiner—M. C. Eakin
Attorney, Agent, or Firm—Mason, Kolehmainen, Rathburn & Wyss

[57] ABSTRACT

1-Pyrrole- and 1-pyrrolidine-carboxylic acid derivatives corresponding to the general formula:

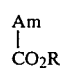

|
$CO_2R$ in which R represents an alkyl radical having from 1 to 4 carbon atoms, preferably ethyl, and Am represents a group:

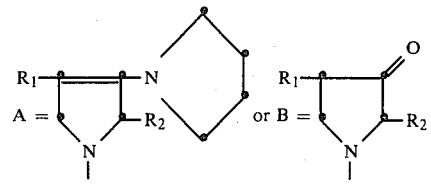

wherein $R_1$ represents a 3-oxo-alkyl radical

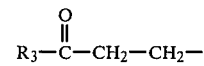

or a 3-oxo-alkenyl radical

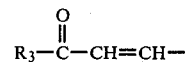

and $R_2$ represents hydrogen or $R_1$ and $R_2$, when they are identical, each represent hydrogen,

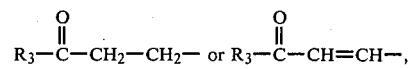

$R_3$ representing an alkyl radical having from 1 to 5 carbon atoms with the proviso that when $R_1$ and $R_2$ are simultaneously hydrogen, Am represents the group A.

The novel derivatives are useful as intermediates for synthetizing azaprostaglandines.

9 Claims, No Drawings

1-PYRROLE- AND 1-PYRROLIDINE-CARBOXYLIC ACID DERIVATIVES AND PROCESS FOR PREPARING THE SAME

This invention relates to novel heterocyclic derivatives and more particularly to novel 1-pyrrole- and 1-pyrrolidine-carboxylic acid derivatives.

The present invention is also concerned with a process for preparing the said novel derivatives.

The derivatives of the invention can be represented by the general formula:

   I in which R represents an alkyl radical having from 1 to 4 carbon atoms, preferably ethyl, and Am represents a group:

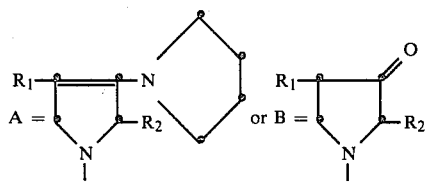

where $R_1$ represents a 3-oxo-alkyl radical

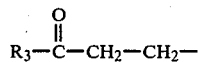

or a 3-oxo alkenyl radical

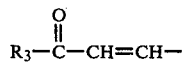

and $R_2$ represents hydrogen or $R_1$ and $R_2$, when they are identical, each represent hydrogen

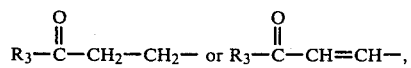

$R_3$ representing an alkyl radical having from 1 to 5 carbon atoms with the proviso that when $R_1$ and $R_2$ are simultaneously hydrogen, Am represents the group A.

Another object of the present invention is to provide a method of using the enamines of formula I wherein Am represents the group A in which $R_1$ and $R_2$ each represent hydrogen and more particularly a method of using ethyl 3-(1'-pyrrolidinyl)-2,5-dihydro-1-pyrrole-carboxylate, as intermediate products for the preparation of other compounds of formula I hereinabove.

The derivatives of formula I can be prepared in accordance with different procedures depending on their chemical structure namely:

(a) an alkyl 3-oxo-1-pyrrolidine-carboxylate of formula:

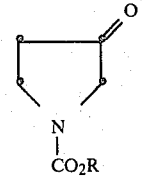   II in which R has the same meaning as cited above is heated in an inert organic solvent, such as, for example, benzene, with pyrrolidine in the presence of p-toluenesulphonic acid and at the reflux temperature of the medium, to obtain the enamines of formula I in which Am represents the group A wherein $R_1$ and $R_2$ each represent hydrogen and more particularly to obtain ethyl 3-(1'-pyrrolidinyl)-2,5-dihydro-1-pyrrole-carboxylate.

(b) an enamine obtained as described above and corresponding to the general formula:

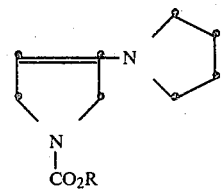   III in which R has the same meaning as previously cited is reacted with an appropriate quantity of a ketone of the general formula:

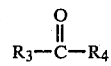   IV in which $R_3$ has the same meaning as in formula I and $R_4$ represents $CH=CH_2$ or $C≡CH$, the reaction taking place in an inert organic solvent such as ethyl ether or benzene at a temperature between 10° and 100° C. to obtain the enaminoketones or enaminodiketones of formula I in which Am represents the group A in which $R_1$ represents $R_3—CO—CH_2—CH_2—$ or $R_3—CO—CH=CH—$ and $R_2$ represents hydrogen or in which $R_1$ and $R_2$ are identical and each represents $R_3—CO—CH_2—CH_2—$ or $R_3—CO—CH=CH—$, (c) the enaminoketone or enaminodiketone, obtained as described above, and corresponding to the general formula:

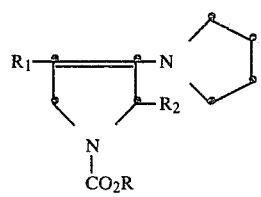   V in which R has the same meaning as previously cited, $R_1$ represents a $R_3—CO—CH_2—CH_2—$ or $R_3—CO—CH=CH—$ radical and $R_2$ represents hydrogen or $R_1$ and $R_2$, when they are identical, each represent a $R_3—CO—CH_2—CH_2—$ or $R_3—CO—CH=CH—$ radical, $R_3$ having the same meaning as in formula I, the hydrolysis taking place in water by means of an acetic acid/alkali metal acetate buffer solution such as a 1 M-aqueous solution of, for example, acetic acid and sodium acetate, at a temperature between 10° C. and the reflux temperature of the medium, which provides the alkyl 3-oxo-1-pyrrolidine-carboxylates of formula I namely the compounds of formula I in which Am represents the group B.

The compound of formula II wherein R represents ethyl, namely ethyl 3-oxo-1-pyrrolidine-carboxylate, is a known compound having been published in J. Am. Chem. Soc., 84, 630 (1962). The other compounds of formula II can be obtained in accordance with the same method as that described in this reference.

With regard to the ketones of formula III, those compounds are for the most part known products or products which can be prepared by known processes.

For example, 1-octyn-3-one has been described in Agr. Biol. Chem. 1969, 33 (9) p. 1264–9, 1-octen-3-one in J. Org. Chem. 22 p. 92–93 (1957), methylvinylketone in J. Soc. Chem. Ind. 29 p. 1037 (1910) and methyl ethynyl ketone in J. Am. Chem. Soc. 72 p. 494–500 (1950)

The compounds of formula I are very valuable intermediate products for use in chemical synthesis.

As has been described in detail above, the compounds of formula I wherein Am represents the group A in which $R_1$ and $R_2$ are each hydrogen are very easy to use for example for the preparation of the other 1-pyrrole-carboxylic acid derivatives of the invention namely the other compounds of formula I wherein Am represents the group A.

These other 1-pyrrole-carboxylic acid derivatives are also particularly valuable intermediate products. For instance the 1-pyrrolidine-carboxylic acid derivatives of the invention namely the compounds of formula I in which Am represents the group B can be obtained through the mere hydrolysis, as described above, of such intermediate products.

Finally, the 1-pyrrolidine-carboxylic acid derivatives of formula I are also very valuable intermediate products.

These compounds are particularly useful as intermediate products for synthetizing azaprostaglandines.

This use is quite unexpected when considered in the light of the intermediate products described in U.S. Pat. No. 4,003,911 for preparing azaprostaglandines.

These intermediates are, in fact, 1-(p-phenylbenzoyl)-2-(carbomethoxyalkyl)-3-oxo-4-acetoxy-1-pyrrolidines which present, therefore, a chemical structure which is quite different from that of the compounds of formula I particularly with respect to the radicals attached to the 1-, 2-, and 4- positions of the pyrrolidine moiety.

The non-limitative Examples which follow illustrate the preparation of the compounds of the invention:

EXAMPLE 1

Preparation of ethyl 3-(1'-pyrrolidinyl)-2,5-dihydro-1-pyrrole-carboxylate (AM=A with $R_1=R_2=H$)

In 50 ml of anhydrous benzene 17.7 g (0.113 mol) of ethyl 3-oxo-1-pyrrolidine-carboxylate were dissolved and then 10 g (0.141 mol) of pyrrolidine followed by 0.1 g of p-toluenesulphonic acid were added. In a Dean-Stark apparatus the reaction mixture was heated to the reflux temperature of the medium for 12 hours under nitrogen atmosphere so that the water was eliminated by azeotropic distillation. The benzene was then evaporated off and the residue was distilled under nitrogen atmosphere.

In this manner, 9.7 g of ethyl 3-(1'-pyrrolidinyl)-2,5-dihydro-1-pyrrole-carboxylate were obtained in the form of a liquid which was kept under nitrogen atmosphere in a refrigerator.

Yield: 41%; B.P.: 138° C. under 0.5 mm Hg

EXAMPLE 2

Preparation of ethyl 4-(3'-oxo-butyl)-3-(1'-pyrrolidinyl)-2,5-dihydro-1-pyrrole-carboxylate (Am=A with $R_1=CH_3-CO-CH_2-CH_2-$ and $R_2=H$)

At room-temperature 0.7 g (0.01 mol) of freshly distilled methylvinylketone dissoled in 20 ml of ether was added drop-by-drop to a solution of 2.1 g (0.01 mol) of ethyl 3-(1'-pyrrolidinyl)-2,5-dihydro-1-pyrrole-carboxylate in 20 ml of ether. The reaction was carried out under inert atmosphere (nitrogen or argon) and protected from light and the mixture was stirred for 6 hours. The ether was then eliminated under vacuum.

In this manner, ethyl 4-(3'-oxo-butyl)-3-(1'-pyrrolidinyl)-2,5-dihydro-1-pyrrole-carboxylate was obtained in crude form.

EXAMPLE 3

Preparation of ethyl 4-(3'-oxo-butyl)-3-oxo-1-pyrrolidine-carboxylate (Am=B with $R_1=CH_3-CO-CH_2-CH_2-$ and $R_2=H$)

The ethyl 4-(3'-oxo-butyl)-3-(1'-pyrrolidinyl)-2,5-dihydro-1-pyrrolecarboxylate, obtained in the previous Example, was treated in crude form with 10 ml of an acetic buffer solution prepared from one mole of acetic acid and one mole of sodium acetate dissolved in one liter of water. The treatment was carried out by stirring the mixture for 2 hours at 20° C. The reaction medium was neutralized by adding sodium carbonate and extracted with methylene chloride. The organic layer was separated out, washed several times with water and then dried on sodium sulphate. The solvent was evaporated under reduced pressure and the residue was taken up by means of a 10/1 ethyl acetate/hexane mixture.

The solution so obtained was then chromatographed on a silica gel column and the solvents were further evaporated off.

In this manner, 1.07 g of ethyl 4-(3'-oxo-butyl)-3-oxo-1-pyrrolidine-carboxylate was obtained in the form of an oily product.

Yield: 47%; $n_D^{20}=1.501$.

Infra-red absorption spectrum (in CCl$_4$): νmax.: 1750 cm$^{-1}$ (C=O of the cycle); 1710 cm$^{-1}$ (C=O of the side chain and of —COO—).

Nuclear magnetic resonance spectrum (in CDCl$_3$): δ=1.3 ppm (t, C$\underline{H}_3$CH$_2$);

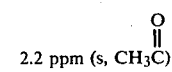

2.2 ppm (s, CH$_3$C)

2.7 ppm (m, CH$_2$); 4.2 ppm (q, C$\underline{H}_2$CH$_3$).

Thin layer chromatography: support: Merck F 254; solvent and eluent: ethyl acetate; revelator: UV and iodine; Rf=0.5.

EXAMPLE 4

Preparation of ethyl 4-(3′-oxo-octyl)-3-(1′-pyrrolidinyl)-2,5-dihydro-1-pyrrole-carboxylate (Am=A with $R_1=C_5H_{11}-CO-CH_2-CH_2-$ and $R_2=H$)

To a solution of 2.1 g (0.01 mol) of ethyl 3-(1′-pyrrolidinyl)-2,5-dihydro-1-pyrrole-carboxylate in 20 ml of benzene was added, under argon atmosphere, a solution of 1.26 g (0.01 mol) of 1-octen-3-one in 20 ml of benzene. The mixture was then heated under reflux for 4 hours and the solvent was evaporated off.

In this manner, ethyl 4-(3′-oxo-octyl)-3-(1′-pyrrolidinyl)-2,5-dihydro-1-pyrrole-carboxylate was obtained in crude form.

EXAMPLE 5

Preparation of ethyl 4-(3′-oxo-octyl)-3-oxo-pyrrolidine-carboxylate (Am=B with $R_1=C_5H_{11}-CO-CH_2-CH_2-$ and $R_2=H$)

The ethyl 4-(3′-oxo-octyl)-3-(1′-pyrrolidinyl)-2,5-dihydro-1-pyrrole-carboxylate obtained in crude form in the foregoing example was hydrolysed in 2 hours at room-temperature by adding 10 ml of the 1 M-acetic buffer solution described in the foregoing Example 3.

The medium was neutralized by adding sodium carbonate and then extracted with methylene chloride. The organic layer was separated out, washed several times with water and then dried over sodium sulphate. The solvent was evaporated off under reduced pressure and the residue was taken up in a 10/1 ethyl acetate/hexane mixture.

This solution was chromatographed on a silica gel column and the solvents were eliminated.

In this manner, 1.16 g of ethyl 4-(3′oxo-octyl)-3-oxo-1-pyrrolidine-carboxylate were obtained in the form of an oily product.

Yield: 41%; $n_D^{20}=1.486$.

Infra-red absorption (in $CCl_4$): νmax.: 1750 cm$^{-1}$ (C=O of the cycle);

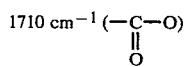

1670 cm$^{-1}$ (C=O of the side chain)

Nuclear magnetic resonance spectrum (in CDCl$_3$): δ=0.9 ppm (t, C$\underline{H}_3$); 1 to 2 ppm (m, CH$_2$ of the side chain, C$\underline{H}_2$ of the cycle, C$\underline{H}_3$—CH$_2$); 4.3 ppm (q, CH$_3$—CH$_2$ and N—CH$_2$) 2.2 ppm (t, C$\underline{H}_2$CO).

Thin layer chromatography: support: Merck F 254; solvent and eluent: ethyl acetate; revelator: UV and iodine; Rf=0.56.

EXAMPLE 6

Preparation of ethyl 4-(3′-oxo-1′-octenyl)-3-(1′-pyrrolidinyl)-2,5-dihydro-1-pyrrole-carboxylate (Am=A with $R_1=C_5H_{11}-CO-CH=CH-$ and $R_2=H$)

To a solution of 2.1 g (0.01 mol) of ethyl 3-(1′-pyrrolidinyl)-2,5-dihydro-1-pyrrole-carboxylate in 20 ml of ether was added slowly and under stirring a solution of 1.24 g (0.01 mol) of 1-octyn-3-one in 20 ml of ether. The reaction was exothermic. Stirring was maintained for 2 hours. After the ethereal solution was cooled to about −5° C., the desired product crystallised. The precipitate was suction-filtered and dried.

In this manner, 1.9 g of ethyl 4-(3′-oxo-1′-octenyl)-3-(1′-pyrrolidinyl)-2,5-dihydro-1-pyrrole-carboxylate were obtained.

Yield: 57.5%; M.P.: 118° C.

Infra-red absorption spectrum (in CCl$_4$): νmax.: 1710 cm$^{-1}$ (—O—C=O); 1670 cm$^{-1}$ (—C=O of the side chain); 1600 cm$^{-1}$ (—C=C—);

Nuclear magnetic resonance spectrum (in CDCl$_3$) δ=0.9 ppm (t, C$\underline{H}_3$) 1.25 ppm (t, C$\underline{H}_3$CH$_2$ and CH$_2$ of the chain) 1.85 and 3.05 ppm (t, CH$_2$ pyrrolidine) 2.3 ppm (t, C$\underline{H}_2$CO) 4.1 ppm (q, COOC$\underline{H}_2$CH$_3$) 5.4 ppm (d, C=C—$\underline{H}$);

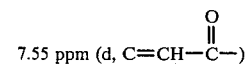

EXAMPLE 7

Preparation of ethyl 2,4-di-(3′-oxo-butyl)-3-(1′-pyrrolidinyl)-2,5-dihydro-1-pyrrole-carboxylate (Am=A with $R_1=R_2=CH_3-CO-CH_2-CH_2-$)

To a solution of 2.1 g (0.01 mol) of ethyl 3-(1′-pyrrolidinyl)-2,5-dihydro-1-pyrrole-carboxylate in 20 ml of ether was added drop-by-drop, at room-temperature, a solution of 2.1 g (0.03 mol) of methylvinylketone in 20 ml of ether. This operation took place under nitrogen atmosphere and was protected from light. Stirring was maintained for 6 hours and, after the solvent was eliminated, the residue was taken up in an ethyl ether/petroleum ether mixture in which it crystallized. The precipitate was then separated out by filtration.

In this manner, 1.5 g of ethyl 2,4-di-(3′-oxo-butyl)-3-(1′-pyrrolidinyl)-2,5-dihydro-1-pyrrole-carboxylate were obtained in the form of a pale yellow solid.

Yield: 43%.

M.P.: 109° C. after recrystallization from a 95/5 ethyl ether/petroleum ether mixture.

Infra-red absorption spectrum (in CCl$_4$) νmax.: 1710 cm$^{-1}$ (O—C=O and C=O); 1640 cm$^{-1}$ (C=C).

Nuclear magnetic resonance spectrum (in CDCl$_3$) δ=1.25 ppm (t, CH$_3$CH$_2$); 1.8 ppm (m, CH$_2$ of the cycle and side chains); 2.15 ppm (s, CH$_3$CO); 3.05 and 3.4 ppm (t, CH$_2$ of the pyrrolidine); 4.15 ppm (q, CH$_2$—CH$_3$).

EXAMPLE 8

Preparation of ethyl 2,4-di-(3′-oxo-butyl)-3-oxo-1-pyrrolidine-carboxylate (Am=B with $R_1=R_2=CH_3-CO-CH_2-CH_2-$)

By heating under reflux for one hour, 1.5 g of ethyl 2,4-di-(3′-oxo-butyl)-3-(1′-pyrrolidinyl)-2,5-dihydro-1-pyrrole-carboxylate, obtained in the preceding Example, were hydrolysed with 10 ml of the 1 M-acetic buffer solution described in Example 3.

The medium was neutralized by adding sodium carbonate and extracted with methylene chloride.

The organic solution was washed several times with water and dried on sodium sulphate. After the solvent was eliminated, the yellow oil so obtained was taken up in a small amount of anhydrous ethyl ether. The medium was cooled to 0° C. and, the yellowish precipitate was filtered out and recrystallized from a 95/5 ethyl ether/petroleum ether mixture.

In this manner, 1.03 g of ethyl 2,4-di-(3'-oxo-butyl)-3-oxo-1-pyrrolidine-carboxylate were obtained.

Yield: 83%.

M.P.: 104° C.

Infra-red absorption spectrum (film). νmax: 1750 cm$^{-1}$ (C=O, cycle); 1710 cm$^{-1}$ (C=O in side chains and O—C=O).

Nuclear magnetic resonance spectrum (in CDCl$_3$) δ=1.3 ppm (t, CH$_3$CH$_2$); 1.35 ppm (m, CH$_2$ side chains); 2.15 ppm (s, CH$_3$CO); 2.4 ppm (t, NCH$_2$); 4.2 ppm (t, NCH and CH$_2$CH$_3$).

We claim:

1. 2,5-Dihydro-1-pyrrole-carboxylic acid derivatives corresponding to the formula:

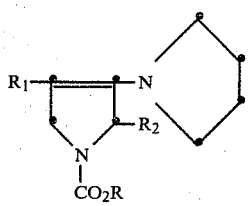

wherein R represents an alkyl radical having from 1 to 4 carbon atoms, R$_1$ represents a 3-oxo-alkyl radical

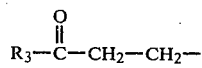

or a 3-oxo-alkenyl radical

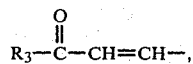

R$_2$ represents hydrogen or R$_1$ and R$_2$, when they are identical, each represents

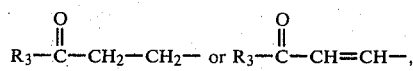

R$_3$ representing an alkyl radical having from 1 to 5 carbon atoms.

2. Ethyl 3-(1'-pyrrolidinyl)-2,5-dihydro-1-pyrrole-carboxylate.

3. Ethyl 4-(3'-oxo-butyl)-3-(1'-pyrrolidinyl)-2,5-dihydro-1-pyrrole-carboxylate.

4. Ethyl 4-(3'-oxo-butyl)-3-oxo-1-pyrrolidine-carboxylate.

5. Ethyl 4-(3'-oxo-octyl)-3-(1'-pyrrolidinyl)-2,5-dihydro-1-pyrrole-carboxylate.

6. Ethyl 4-(3'-oxo-octyl)-3-oxo-1-pyrrolidine-carboxylate.

7. Ethyl 4-(3'-oxo-1'-octenyl)-3-(1'-pyrrolidinyl)-2,5-dihydro-1-pyrrole-carboxylate.

8. Ethyl 2,4-di-(3'-oxo-butyl)-3-(1'-pyrrolidinyl)-2,5-dihydro-1-pyrrole-carboxylate.

9. Ethyl 2,4-di-(3'-oxo-butyl)-3-oxo-1-pyrrolidine-carboxylate.

* * * * *